United States Patent
Dragan

(10) Patent No.: US 6,890,177 B2
(45) Date of Patent: May 10, 2005

(54) METHOD AND DEVICE FOR THE RETRACTION AND HEMOSTASIS OF TISSUE DURING CROWN AND BRIDGE PROCEDURES

(75) Inventor: William B. Dragan, Easton, CT (US)

(73) Assignee: Centrix, Inc., Shelton, CT (US)

( * ) Notice: Subject to any disclaimer, the term of this patent is extended or adjusted under 35 U.S.C. 154(b) by 8 days.

(21) Appl. No.: 10/307,695

(22) Filed: Dec. 2, 2002

(65) Prior Publication Data

US 2004/0106086 A1 Jun. 3, 2004

(51) Int. Cl.$^7$ .................................................. A61C 5/14
(52) U.S. Cl. ......................................... 433/136; 433/214
(58) Field of Search .............................. 433/34, 37, 38, 433/39, 136, 214

(56) References Cited

U.S. PATENT DOCUMENTS

| | | | | |
|---|---|---|---|---|
| 2,396,203 A | * | 3/1946 | Robinson | 606/201 |
| 2,620,502 A | * | 12/1952 | Russak | 15/244.4 |
| 3,056,205 A | * | 10/1962 | Ennor | 433/35 |
| 3,705,585 A | * | 12/1972 | Saffro | 604/385.01 |
| 4,071,955 A | * | 2/1978 | Julius | 433/136 |
| 4,173,219 A | * | 11/1979 | Lentine | 604/77 |
| 4,531,914 A | * | 7/1985 | Spinello | 433/136 |
| 5,676,543 A | | 10/1997 | Dragan | |
| 5,980,249 A | * | 11/1999 | Fontenot | 433/80 |

* cited by examiner

Primary Examiner—Todd E. Manahan
(74) Attorney, Agent, or Firm—Fattibene & Fattibene; Paul A. Fattibene; Arthur T. Fattibene

(57) ABSTRACT

A method and a device for effecting the cordless retraction of the gingival sulcus tissue prior to the taking of an impression of a tooth for making a crown or bridge which is attained by controlling any bleeding in the gingival sulcus area, and utilizing a dental dam preferably formed of a sponge or foam like material to contain an astringent fortified silicone impression material embedded about the prepared tooth, and using the patient's biting force to apply the necessary pressure onto the dam until the silicone impression material sets and adheres to the dam to enhance easy removal of the set impression material from the tooth. The dam is formed to accommodate either the posterior teeth or the anterior teeth.

14 Claims, 3 Drawing Sheets

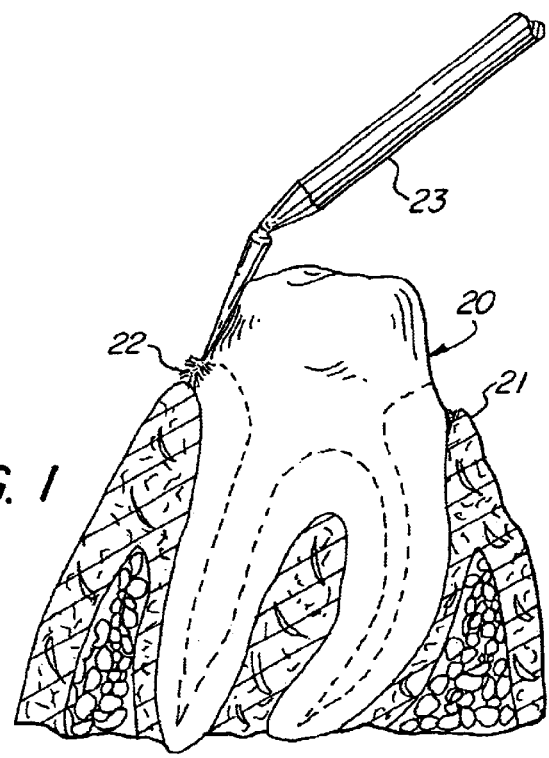
FIG. 1
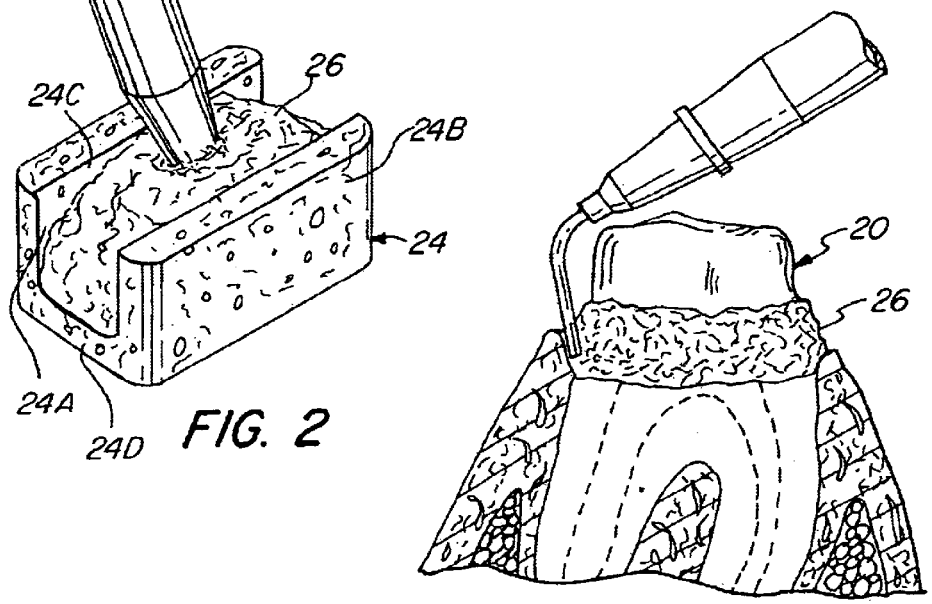
FIG. 2
FIG. 3

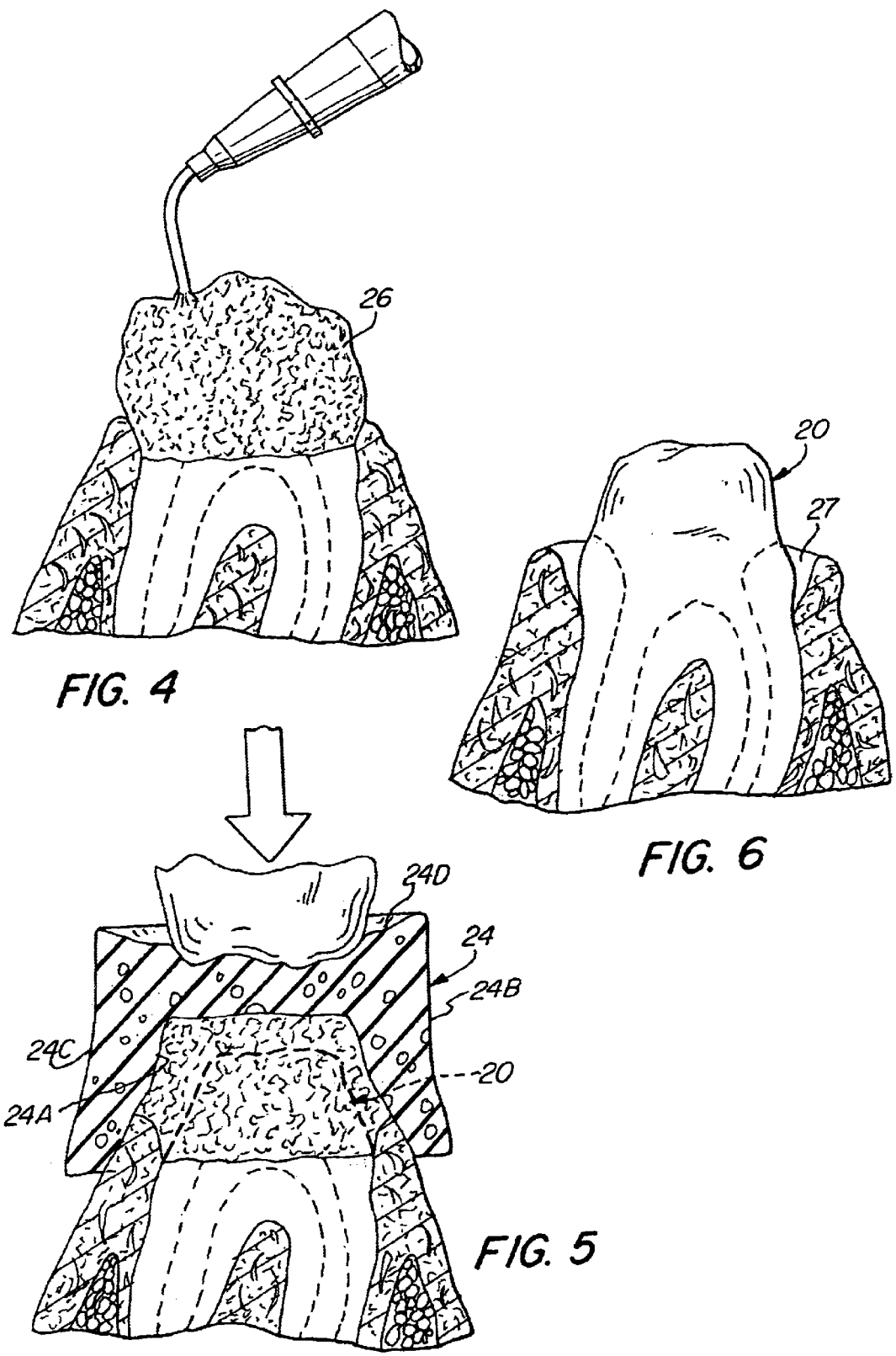

US 6,890,177 B2

METHOD AND DEVICE FOR THE RETRACTION AND HEMOSTASIS OF TISSUE DURING CROWN AND BRIDGE PROCEDURES

FIELD OF THE INVENTION

This invention is directed to a method and device for effecting hemostasis retraction of tissue, and more specifically to a method and device for the retraction and hemostasis of tissue in preparing a tooth prior to the taking of an impression for forming a crown or bridge dental prosthesis.

BACKGROUND OF THE INVENTION

The traditional method for controlling hemostasis and retraction of gingival tissue prior to the taking of an impression of a prepared tooth to form a crown or bridge is to mechanically pack a small length of cord saturated with an astringent about the base of the tooth to enlarge the gingival sulcus space about the base of a tooth. After a period of time, the cord is removed from the enlarged space defined about the base of the tooth. Upon the removal of the cord, it frequently happens that coagulum formed to stop the bleeding or seepage of fluid is removed with the cord to result in the seepage of additional bleeding into the space. As a result, an impression cannot be made of the prepared tooth until the additional bleeding can be controlled or stopped. Thus, the traditional procedure for enlarging the space between the gum and the base of the tooth necessary for taking an accurate impression is tedious, time consuming and painful or extremely uncomfortable for the patient. Also, there exists the danger that the dentist may accidentally force the cord beyond the physiologic limit of the space to create a potential periodontal pocket which can cause the tooth to be eventually lost. The general practice of using the cord technique is relatively difficult and tedious for the dentist. In the event that the space between the tooth and the gum that has to be retracted is very small, it becomes even more difficult for the dentist to place the cord without injuring the gum tissue and from forcing the cord beyond the physiologic limit, and renders the procedure more painful for the patient. Further, the placing of the cord is not a procedure which the dentist may delegate to a dental assistant or dental hygienist. Also, the packing of a retraction cord is a most disliked step to perform during a crown or bridge restoration procedure.

Efforts have been made to obviate the noted disadvantages of affecting the retraction of the gingival tissue by the use of a cord. One such known effort is the use of a kaolin type material that is mixed with an astringent salt which is simply placed about a prepared tooth to absorb the moisture to cause the gum tissue to shrink. Such a product is marketed by Sybron Dental Specialties under the brand name EXPA-SYL.

It has been noted that such kaolin type material is packaged in a cartridge similar to a typical anesthetic cartridge commonly used in a dental office that requires the cartridge to be used with a syringe. The end of the cartridge is pierced with a needlelike cannula and the force of the syringing pressure is required to extrude the clay like kaolin material through the cannula. Because of the density of the kaolin type material, the cannula requires the opening to be very large so as to enable the kaolin type material to flow therethrough. The large guage opening of the cannula renders the bending of the cannula difficult and which bending is often required in order to place the material in difficult to reach places within a patient's mouth. Because the opening of the cannula is quite large, difficulty is encountered in placing the kaolin type material about the gingival sulcus in a manner similar to the traditional method of packing cord to retract the gum tissue. Use of such kaolin type material to retract the gum tissue tends to crumble, rendering it difficult to place in the space between the gum tissue and the tooth to attain the desired retraction of the gum tissue. Another noted problem with such kaolin type material is the removal of the kaolin material after the period of time required to affect the hemostasis and the retraction. Generally, the kaolin material is required to be washed out using a water-air spray with extreme care to remove all the kaolin material without restarting any bleeding in the gingival sulcus.

Another known technique for effecting a non-cord retraction and hemostasis is disclosed in my prior U.S. Pat. No. 5,676,543. Therein disclosed is a generally two part process utilizing two different viscosities of a condensation silicone material to effect the cordless retraction and hemostasis of the gingival sulcus.

This invention is directed to an improvement to the non-cord retraction and hemostasis procedure described in my prior U.S. Pat. No. 5,676,543. This invention is directed to a more simplified non-cord retraction and hemostasis process and a device for accomplishing the same.

SUMMARY OF THE INVENTION

An object of this invention is to provide a one part cordless retraction method for enlarging the gingival sulcus space between the gum tissue and the prepared tooth prior to the taking of an impression during a crown or bridge procedure.

Another object is to provide a foam, rubber or sponge like dam for effecting the cordless retraction and hemostasis of the gingival sulcus of a prepared tooth prior to the taking of an impression.

Another object is to provide for a hemostasis and cordless retraction of the gingival sulcus using the patient's own biting pressure to force the retraction material into the space between the gum tissue and the prepared tooth to enlarge the same.

Another object is to provide a cordless hemostasis and retraction method which is positive in operation and simple to perform.

Another object is to provide for a cordless hemostasis retraction method of the gingival sulcus area, which is painless, comfortable and easy on the patient, and easy for the dentist to perform.

The foregoing objects and other features are attained by the method of first preparing a tooth to be restored for taking an impression thereof in preparation of forming a crown or bridge. After the tooth has been properly prepared and before a proper impression can be made, the gum tissue about the base of the tooth must be retracted so as to enlarge the gingival sulcus. This is achieved in accordance with this invention by the injection of a suitable liquid astringent about the base of the tooth to control or stop any excessive bleeding or seepage of fluid. This can be attained by the application of a liquid hemostasis agent, e.g. aluminum chloride, ferric sulfate and the like to the cut tissue by syringing or other suitable applicator. Where bleeding is slight or minimal, it may not be necessary to apply any astringent. After the controlled hemostasis, a foam or sponge like dam having a groove or trough is adjusted and fitted so as to cover at least one tooth mescal and distal beyond the prepared tooth. The foam or sponge dam so formed is then filled with a silicone type impression material which is fortified with a hemostatic agent. A predetermined amount of the fortified silicone impression material is also placed about the entire circumference of the prepared tooth at the gingival sulcus margin, preferably by syringing. The application of the silicone impression material is then generously applied to cover the entire prepared tooth. The sponge or foam dam filled with the silicone impression material is then placed over the silicone covered tooth, at which time the patient is instructed to apply a biting pressure onto the sponge or foam dam and to maintain the biting pressure thereon for a predetermined time period sufficient for the silicone-impression material to set, e.g. 5 to 7 minutes. The sponge or foam dam is then removed together with the set or cured silicone material which remains adhered to the sponge or foam dam. Upon removal of the dam, the tooth may be lightly washed and examined in preparation of the taking of the impression. If additional retraction of the gum tissue is required, the procedure may be repeated.

IN THE DRAWINGS

FIG. 1 is a side view of a prepared tooth and illustrating the placement of a liquid hemostatic agent to control bleeding about the gingival sulcus area.

FIG. 2 illustrates the filling of the groove of a sponge or foam dam for use on posterior teeth with an amount of impression material.

FIG. 3 illustrates the intermediate step of placing the silicone impression material about the gingival sulcus area.

FIG. 4 illustrates the generous application of the silicone impression material covering the entire prepared tooth.

FIG. 5 illustrates the step of placing the filled sponge or foam dam onto the covering of the prepared tooth and the application of a biting pressure thereon.

FIG. 6 is a view similar to that of FIG. 5 to illustrate the retraction and enlargement of the space between the retracted gum tissue and the base of the prepared tooth with the dam and impression material removed.

DETAILED DESCRIPTION

Figure 7:
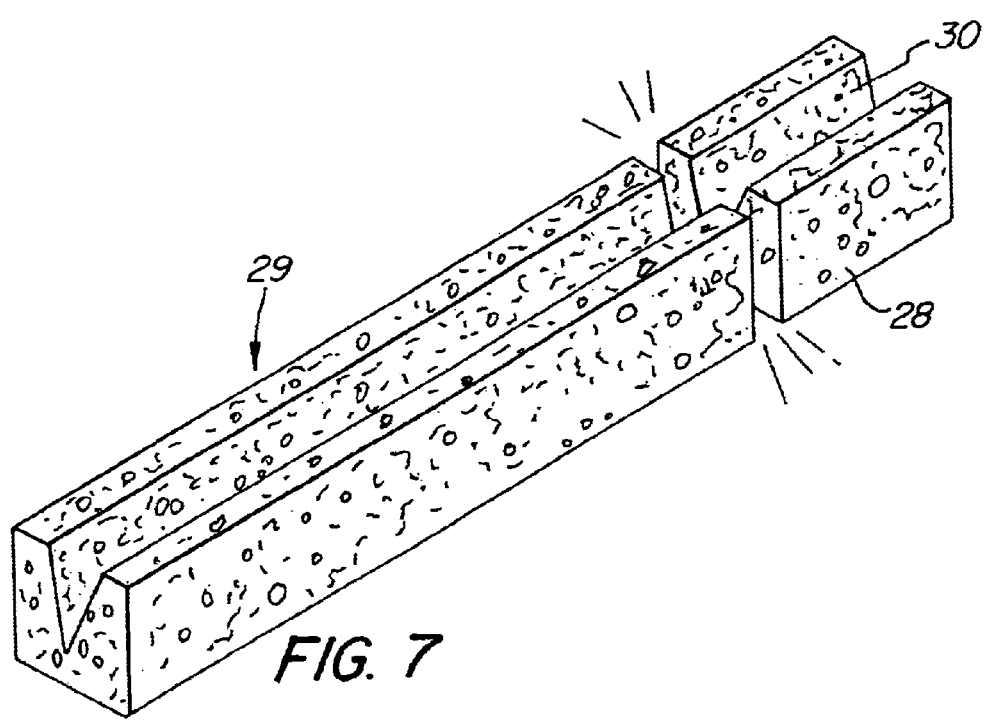
FIG. 7 illustrates a perspective view of a slightly modified sponge or foam dam for use in the cordless retraction of the gum tissue about anterior teeth.

Referring to the drawings, there is shown a tooth 20 which has been prepared for receiving a crown or bridge. However, before the impression can be taken for preparing the crown or bridge, it is imperative that the gingival sulcus tissue 21 be retracted in order for the dentist to make an accurate impression of the prepared tooth 20. In accordance with this invention and to control any excessive gingival bleeding, an application of a liquid hemostatic agent 22, e.g. aluminum chloride, ferric sulfate or other suitable astringent is applied to the cut tissue in the area of the gingival sulcus. The astringent can be applied with Centrix's Benda micro applicator 23 as seen in FIG. 1, or by any other suitable applicator, e.g. Centrix, Inc.'s BENDA® brush, SoftStix™ disposable applicator, or syringe, and the like. The astringent 22 is applied with moderate pressure and by rubbing the astringent solution against the cut tissue to infuse the astringent solution into the cut capillaries. After the bleeding is under control, a dam 24 is adjusted and fitted to the prepared tooth 20 and to at least one tooth mescal and distal beyond the prepared tooth or teeth 20.

In accordance with this invention, the dam 24 is formed of a porous foam or sponge type material which may be either natural or synthetic. The dam 24, as shown in FIG. 4, is formed for use on posterior teeth.

As shown, the dam 24 may be formed as an elongated block of a sponge, foam, or other type of porous material. It will be understood that the block of foam or sponge may be of any desired length from which the dentist may sever therefrom the desired length necessary to dam one or more teeth being worked upon. Conversely, the dam 24 may be pre-cut to size, depending upon the number of teeth that may require gum retraction and to which the finished crown or bridge is to be applied. As seen in FIG. 4, the foam or sponge dam 24 is provided with a longitudinally U-shaped groove or trough 24A extending along the length thereof. The respective opposed side walls 24B and 24C and interconnected web or bottom 24D, as shown in FIG. 4, are sufficiently thick to contain and exert the necessary pressure to effect the gum tissue retraction as will be herein described.

FIG. 7 illustrates a modified block of sponge or foam material from which a modified dam construction for use with anterior teeth is formed, as will be hereinafter described.

After the bleeding of the gum tissue to be retracted is controlled, the groove 24A of an appropriate size dam 24 is filled with a hereinbefore described fortified silicone type impression material 26, as shown in FIG. 2. The silicone material 26 may comprise a two-part composition which includes a base portion and a catalyst portion which, when mixed, will quickly set and become solid. The time of setting can be varied within a predetermined time range by controlling the ratio of catalyst to base. Such silicones are available from various manufacturers, e.g. CONQUEST by Pentron, EXAFLEX by G.C., EXTRUDE by Kerr Corporation or IMPRESS and EXPRESS by 3M Corporation. While the silicone materials are preferred, other materials such as polyethers, polysulfides and any other dental moldable materials may be used. The condensation silicone materials are preferred. The silicone material 26 is further fortified with between five percent (5%) to twenty percent (20%) by weight of a suitable astringent to aid in the gum tissue retraction and hemostasis. Any of the known astringents may be used which are rendered compatible with the silicone. Some of the known astringents or hemostasis agents are aluminum potassium sulfate, aluminum sulfate, or alum, ferric sulfate, aluminum ammonionium sulfate, ferric chloride, aluminum chloride, sodium chloride, zinc chloride and others.

The same silicone material is also applied about the gingival sulcus area as shown in FIG. 3, preferably by syringing. The entire prepared tooth 20 is then covered with the same silicone material as shown in FIG. 4. It will be understood that the step of applying the silicone material to the dam 24 or about the tooth as shown in FIGS. 3 and 4 can be reversed. With the tooth covered with the silicone material 26, and with the groove 24A of the dam 24 filled with the same silicone material, the silicone-filled dam 24 is placed onto the silicone covered tooth, as best seen in FIG. 5.

With the filled dam 24 disposed over the silicone covered tooth or teeth, the patient is instructed to apply a biting force or pressure onto the dam 22 as shown in FIG. 5, and to maintain the biting pressure on the dam 24 until such time that the silicone material sets, approximately 5 to 7 minutes. Upon setting of the silicone material, the dam 24 and the set moldable material is removed to expose the prepared tooth as shown in FIG. 6. As the dam 24 is formed of a porous or foam sponge-like material, the silicone material, upon setting, will penetrate the pores of the foam material, causing the set silicone material to mechanically adhere to the dam 24 whereby the set silicone material can be removed in unison upon the removal of the dam 24. The tooth may then be lightly washed, dried and examined to determine if the gum tissue has been sufficiently retracted so as to enable an accurate impression to be made.

The bite pressure imparted by the patient onto the dam 24 as seen in FIG. 5, causes the silicone impression material to be forced into the gingival sulcus space, which together with the interaction of the astringent material causes the gum tissue in the gingival sulcus area to retract to enlarge the space 27 between the tooth and surrounding gum tissue as noted in FIG. 6. In the event additional retraction of the gum tissue is required, the procedure hereinabove described may be repeated.

While the sponge or foam dams 24, as described herein, are preferred, it will be understood that other means may be used in lieu of the foam or sponge dams, e.g. a cotton roll or hollowed cotton gauze or pad, or other suitable material capable of containing the silicone, astringent based, material when the biting pressure is applied and maintained. The use of the biting pressure on the dam 24 causes the silicone material containing the astringent material to be forced onto the gingival sulcus space, causing the gum tissue to be retracted an amount sufficient to permit an accurate tooth impression to be made for making a crown or bridge.

While the method described is in reference to retracting the gum tissue of a posterior tooth, the same method is applicable for retracting the gum tissue of an anterior tooth. However, for an anterior gum retraction, the dam is preferably constructed with a V-shaped groove, as in FIG. 7.

Referring to FIG. 7, an anterior dam 28 may be severed from an elongated block 29 of foam or sponge like material similar to that hereinbefore described, except the groove 30 is generally V-shaped as shown in FIG. 7. The opposed sides of the V-shaped groove 30 converge inwardly of the foam or sponge block. In all other respects, the construction of dam 28 and the use thereof is similar to that described with respect to the construction and use of dam 24. It will be understood that the foam material, from which the described dams are made, may be formed of open or closed cells, natural or synthetic foam or sponge.

The method described and the dam for effecting the same is relatively simple, expedient and results in a positive retraction of the gum tissue so as to ensure that all margins can be captured in a subsequent impression procedure. The described invention further reduces the trauma and discomfort often encountered by the patient in a gum retraction procedure. Also, the present invention provides enhanced results with much greater ease on the part of the dentist. The procedure is rendered so simple that it can be delegated to a dental assistant.

While the preferred embodiments of the present invention have been illustrated and described, it will be obvious to those skilled in the art that various modifications may be made without departing from the spirit and scope of this invention.

What is claimed is:

1. A non-cord method of retracting gum tissue in preparation for taking an impression comprising:
   (a) preparing a tooth for restoration;
   (b) controlling any bleeding occurring with respect to any cut tissue in the gingival sulcus area;
   (c) placing an amount of an impression material into the groove of a dental dam made of a porous material;
   (d) covering the prepared tooth with a layer of said impression material;
   (e) placing the trough of the dental dam filled with the impression material onto the prepared tooth covered with the impression material;
   (f) requiring the patient to apply a biting pressure onto the dental dam;
   (g) permitting the impression material to penetrate the porous material of the dental dam;
   (h) maintaining the biting pressure on the dental dam until the impression material has set; and
   (i) removing the dental dam with the impression material attached from within the patient's mouth.

2. A non-cord method of retracting gum tissue as defined in claim 1 wherein steps (c) and (d) may be reversed.

3. A non-cord method of retracting gum tissue as defined in claim 1 wherein the dental dam is formed of a porous foam material.

4. A non-cord method of retracting gum tissue as defined in claim 3 wherein:
   said dental dam is formed as an elongated block of said foam material having a groove extending longitudinally of said block, and said block being of sufficient thickness to retain the impression material confined within said groove when a biting pressure is applied thereto.

5. A non-cord method of retracting gum tissue as defined in claim 1 wherein said impression material used comprises a two-part composition which includes a base portion and a catalyst portion which, when mixed, will quickly set.

6. A non-cord method of retracting gum tissue as defined in claim 5 wherein said composition used is fortified with an astringent selected from the group consisting of aluminum potassium sulfate, potassium aluminum sulfate, aluminum sulfate, alum, ferric sulfate, aluminum ammonionium sulfate, ferric chloride, aluminum chloride, sodium chloride and zinc chloride.

7. A non-cord method of retracting gum tissue for taking a tooth impression comprising:
   (a) controlling any bleeding occurring with respect to any cut tissue in the gingival sulcus area;
   (b) covering the prepared tooth with a generous amount of impression material;
   (c) placing the groove of a dental dam made of a porous material onto the prepared tooth covered with the impression material;
   (d) requiring the patient to apply a biting pressure onto the dental dam;
   (e) permitting the impression material to penetrate the porous material of the dental dam;
   (f) maintaining the biting pressure on the dental dam until the impression material has set;
   (g) removing the dental dam with the impression material attached from within the patient's mouth.

8. A non-cord method of retracting gum tissue as defined in claim 7 wherein said dental dam is formed of a cellular foam material.

9. A non-cord method of retracting gum tissue in preparation for taking a tooth impression comprising:
   (a) placing an amount of an impression material into the groove of a dental dam made of a porous material;
   (b) covering the prepared tooth with a layer of said impression material;
   (c) placing the trough of the dental dam filled with the impression material onto the prepared tooth covered with said impression material;

(d) requiring the patient to apply a biting pressure onto dental dam;

(e) permitting the impression material to penetrate the porous material of the dental dam;

(f) maintaining the biting pressure on the dental dam until the impression material has set;

(g) removing the dental dam with the impression material attached from within the patient's mouth.

10. A device for effecting the cordless retraction of gum tissue comprising:

a block of a porous cellular material of a size to receive a prepared tooth;

said block having a groove extending co-extensively thereof to form a dental dam;

said groove being adapted to receive the prepared tooth; and an initially flowable material placed within said groove of said block of the porous cellular material, whereby the initially flowable material penetrates the pores of the porous cellular material so that upon setting adheres to the block of the porous cellular material.

11. A device as defined in claim 10 wherein said groove is U-shaped, and said dental dam having opposed side walls defining said groove, said side walls being of sufficient thickness to contain the impression material when a biting force is applied thereto.

12. A device as defined in claim 10 wherein said groove is V-shaped for use with the anterior teeth.

13. A device as defined in claim 10 wherein said cellular material comprises a synthetic foam material.

14. A device as defined in claim 10 wherein said cellular material comprises a sponge.

* * * * *